United States Patent [19]

Escrig et al.

[11] Patent Number: 6,160,138
[45] Date of Patent: Dec. 12, 2000

[54] PROCESS FOR EPOXYDATION OF OLEFINIC COMPOUNDS WITH HYDROGEN PEROXIDE

[75] Inventors: Pilar De Frutos Escrig; José Miguel Campos Martin, both of Madrid, Spain

[73] Assignee: Repsol Quimica, S.A., Madrid, Spain

[21] Appl. No.: 09/424,572

[22] PCT Filed: Mar. 26, 1998

[86] PCT No.: PCT/ES98/00078

§ 371 Date: Feb. 16, 2000

§ 102(e) Date: Feb. 16, 2000

[87] PCT Pub. No.: WO99/48884

PCT Pub. Date: Sep. 30, 1999

[51] Int. Cl.[7] .................................................. C07D 301/12
[52] U.S. Cl. ............................................................ 549/531
[58] Field of Search .............................................. 549/531

[56] References Cited

U.S. PATENT DOCUMENTS

| | | | |
|---|---|---|---|
| 3,923,843 | 12/1975 | Wulff | 260/348.5 L |
| 4,367,342 | 1/1983 | Wulff | 549/529 |
| 4,410,501 | 10/1983 | Taramasso et al. | 423/326 |
| 5,214,168 | 5/1993 | Zajacek et al. | 549/531 |
| 5,374,747 | 12/1994 | Saxton et al. | 549/531 |
| 5,463,090 | 10/1995 | Rodriguez et al. | 549/531 |
| 5,621,122 | 4/1997 | Saxton et al. | 549/529 |

FOREIGN PATENT DOCUMENTS

| | | |
|---|---|---|
| 0 200 260 A2 | 12/1986 | European Pat. Off. . |
| 0 230 949 A2 | 8/1987 | European Pat. Off. . |
| 0 568 336 A2 | 11/1993 | European Pat. Off. . |
| 0 659 685 A1 | 6/1995 | European Pat. Off. . |
| 0 712 852 A1 | 5/1996 | European Pat. Off. . |
| 0 732 327 A1 | 9/1996 | European Pat. Off. . |
| 0 743 094 A1 | 11/1996 | European Pat. Off. . |
| WO 94/23834 | 10/1994 | WIPO . |

OTHER PUBLICATIONS

Clerici, M.G., "Synthesis of Propylene Oxide from Propylene and Hydrogen Peroxide Catalyzed by Titanium Silicalite", journal of Catalysis 129, 159–167 (1991).

Clerici, M. G. et al, "Chapter 5, Clean Oxidation Technologies: New Prospects in the Epoxidation of Olefins", Green Chemistry, ACS Pub. Services, 1996 (pp. 58–68).

Camblor, et al, "Synthesis and Catalytic Activity of Aluminum –free Zeolite Ti beta Oxidation Catalysts"' J. Chem. Soc. Chem Commun., 1996, pp. 1339–1340.

Gorma, et al, "Synthesis of an Ultralarge Pore Titanium Silicate Isomorphous to MCM–41 and its Application as a Catalyst for selective Oxidation of Hydrocarbons" J. Chem. Soc. Chem. Commun. 1994 (pp. 147–148).

*Primary Examiner*—Ba K. Trinh
*Attorney, Agent, or Firm*—John C. McMahon

[57] ABSTRACT

Epoxidation procedure for olefinic compounds with hydrogen peroxide in the presence of solvents, preferably $C_1$–$C_8$ alcohols, using silica supported titanium catalysts, prepared by the impregnation of the silica with solutions of titanium alkoxydes and/or titanocenes in oxygenated organic solvents.

20 Claims, No Drawings

6,160,138

PROCESS FOR EPOXYDATION OF OLEFINIC COMPOUNDS WITH HYDROGEN PEROXIDE

This application is a 371 of PCT/ES98/00078 dated Mar. 26, 1998.

STATE OF THE ART

Epoxides such as ethylene oxide, propylene oxide, glycidol, etc, are intermediate products in the preparation of a wide range of products. For example, epoxides can be hydrolysed to yield glycols used in the formulation of antifreeze fluids or as monomers in the preparation of condensation polymers such as polyesters. Polyols, generated by epoxide ring cleavage polymerisation, are broadly used in the preparation of polyurethane foams, sealant elastomers, linings, etc. The reaction with alcohols yields glycolic ethers that are used as polar solvents in numerous applications.

The epoxidation of olefinic unsaturated compounds can be performed with a wide range of reactants. The epoxidation of olefins in the liquid phase with organic hydroperoxides is particularly interesting, which process is used industrially despite these reactions yielding as co-products the alcohols derived from the hydroperoxides used. On the other hand, the catalytic epoxidation with hydrogen peroxide has not been as successful due to economic factors and to the lack of efficient catalysts. However, in the eighties, an Italian group developed catalyst called titanium silicalytes, microporous solids with the MFI type structure, in which the titanium atoms hold places in the structure of the crystalline lattice, U.S. Pat. Nos. 4,410,501, 4,666,692, 4,701,428, 4,824,976 and 4,833,260. These titanium and silica compounds are known as TS-1, and are effective catalysts for the epoxidation of olefinic compounds with hydrogen peroxide in the presence or in the absence of solvents. Even though the specificity for epoxide is high when the epoxidation is effected in a protic medium such as an alcohol or water it is very important, both for kinetic and specificity reasons, the use of important amounts of methanol as solvent. This alcohol is considered as a co-catalyst (M. G. Clerici et al. J. Catal. 129, 159 (1991), M. G. Clerici et al. in Green Chemistry, ACS Pub. Services, 1996, p. 58). The use of this solvent posses a problem in the epoxidation of polypropylene, due to the fact that it hinders the subsequent purification stages of the product by means of the nearest boiling point between propylene and methanol (European Patent Application no. 673935 A2).

Even though the specificity for epoxide is relatively high, the non selective breaking of the oxiranic ring takes place during the epoxidation reaction. In order to increase the specificity for epoxide the catalyst may be treated with a neutralising agent for the superficial acid sites of the catalyst, responsible for the formation of these undesired byproducts (U.S. Pat. No. 4,824,296, European Patent no. 230949). Subsequently, the European Patent application no. 712852 A1 indicates that this same effect may be achieved when the epoxidation is carried out in the presence of small amounts of non basic salts such as lithium chloride, sodium nitrate, etc.

On the other hand, as a consequence of the small pore size of the titanium silicalytes (5.6×5.3 Å), there exists a wide range of olefins that cannot be epoxidated with these catalysts since voluminous olefins cannot reach the active sites. In order to be able to avoid these limitations several authors have proceeded to the synthesis of zeolytes of larger pore size with titanium in the lattice, such as for instance the beta zeolyte structure (Tiβ) (Spanish Patent application no. 9101798, Camblor et al. in J. Chem. Soc., Chem. Commun., page 589 (1992) and U.S. Pat. No. 5,412,122), but very low specificity for epoxide was obtained due to the presence of acid sites (aluminium) in the lattice which favour the breaking of the oxirane ring. Due to these problems certain authors claim the synthesis of Tiβ compounds without the presence of aluminium in the lattice (U.S. Pat. Nos. 5,374,747 and 5,621,122 and European Patent no. 659685 and Camblor et al. in Chem. Commun., page 1339 (1996)) despite of which, it still shows a very low specificity for epoxide.

The relatively high price of hydrogen peroxide in commercial aqueous solution and the difficulties in the transportation of concentrated solutions have given rise to the proposal for the use of these catalysts in joint processes for the obtaining of epoxides and hydrogen peroxide. Thus, for instance, European Patent no. 526947 describes a process for the production of epoxides, whereby hydrogen peroxide is produced "in situ" by the reaction of oxygen or air with a redox system made up of an alkylhydroanthraquinone, and reacts with the olefin in the presence of a titanium silicalyte catalyst and a specific mixture of solvents, comprising one or several aromatic hydrocarbons, one or more polar organic compounds of a high boiling point and a low molecular weight alcohol (methanol). The precise reasons for the use of complex solvent mixtures are not indicated in the mentioned publication, but it is known that alkylanthraquinones and alkylhydroanthraquinones show a low solubility in common solvents, limiting the maximum amount of hydrogen peroxide which can be generated in a determined reactor's volume. European Patent no. 549013 describes, as well, an epoxidation process for olefins with hydrogen peroxide in the presence of titanium silicalyte which uses a mixture of water-alcohol solvents in order to extract the $H_2O_2$ resulting from an oxidation process of the alkylhydroanthraquinone redox system. As has been indicated above the alkylhydroanthraquinones used have low solubility in solvents which significantly limits the commercial usefulness of the process. U.S. Pat. No. 5,463,090 describes an integrated process for the production of epoxides based on the oxidation of the salts of alkylhydroanthraquinones with a sulfonic acid substituent in order to yield a complex reaction mixture which contains hydrogen peroxide. The product of the oxidation reaction is used in the epoxidation of olefins in the presence of titanium silicalyte as catalyst. In this manner it was claimed that the solubility of alkylhydroanthraquinone salts in different solvents substantially decreases the size of the reactor. U.S. Pat. Nos. 5,214,168 and 5,384,418 and European ones numbers 568336 and 732327 describe processes for the epoxidation of olefins in which by means of the oxidation of secondary alcohols with oxygen or air, hydrogen peroxide and the corresponding ketones are obtained. The $H_2O_2$ solution obtained, or with a subsequent treatment, is used in the epoxidation of olefins using titanium silicalyte as the catalyst and methanol as the solvent. All these epoxidation procedures use molecular sieve type catalysts with titanium in the lattice at the epoxidation stage, which catalysts due to the difficulty in their synthesis have a very high price. These catalysts are rapidly deactivated in the reaction medium and thus it makes it necessary to use inert binders for their use in the industry and ease of re-utilisation (European Patent nº 200 260) or a modification of the preparation method (European Patent no. 638362), which decreases the active stage of the catalyst used.

It is known that silica supported titanium catalysts are effective in the epoxidation of olefins with organic hydroperoxides refer for instance to U.S. Pat. Nos. 3,642,833, 3,923,843, 4,021,454 and 4,367,342. It is believed that in general these catalysts are not effective in the epoxidation of olefins with hydrogen peroxide. However, the patent WO 94/23834 describes silica and titanium based catalysts and their use in a wide range of chemical oxidation reactions, in particular the epoxidation of olefins with hydrogen peroxide or organic hydroperoxides. These catalysts are synthesised by impregnating amorphous silicas with titanium fluorides under certain experimental conditions, although they show moderate specificity for epoxide, for example not above 72%, cf. example 26 in patent WO 94/23834.

Thus, presently the art feels the need to have available new active and specific catalysts for the epoxidation of olefinic unsaturated compounds with hydrogen peroxide, more economical, easy to prepare, easy to regenerate, capable of operating at relatively high temperatures, with high reaction speeds and which do not require the use of methanol as the solvent.

We ourselves, and in a completely unexpected manner, have discovered that these problems of the prior art can be avoided and/or minimised by using silica supported titanium catalysts prepared according to the invention.

DESCRIPTION OF THE INVENTION

The subject matter of the invention is an epoxidation procedure for olefinic unsaturated compounds with hydrogen peroxide in the presence of silica supported titanium catalysts prepared by the impregnation of a silica of a specific surface of 50–900 m$^2$/g with a solution of a titanium alkoxyde or of a titanocene in an organic solvent, followed by the separation of the excess solution by means of known procedures, for instance, by filtration, decanting, centrifuging or evaporation. The solid catalyst thus isolated may undergo, optionally, a drying procedure and preferably an activation pre-treatment before being used in the epoxidation procedure according to the invention. The precise pre-treatment method depends on the nature of the titanium alkoxyde or of the titanocene and of the solvent used but, in general, the pre-treatment consists in the heating of the catalyst initially prepared in the presence of an inert gas such as nitrogen, argon, or carbon dioxide, or in the presence of a gas that contains oxygen, e.g. air, or else a successive treatment in an inert and oxidising atmosphere. A function of the pre-treatment is the transformation of the organic titanium compound used in the impregnation into the corresponding oxide. Thus for instance, the initial components of the catalyst such as titanium isopropoxide or titanium butoxide become titanium oxide in the oxidising or inert atmosphere. The pre-treatment temperature is not critical and may range between 200 and 1000° C., for a time interval between 1 and 48 hours.

Compounds containing at least one oxygen atom in their molecule are preferably used as the organic solvents in the impregnation of silica according to the invention, which compounds are liquid under normal conditions and that in general contain from 1 to 8 carbon atoms in their molecule. For example adequate solvents are alcohols and glycols, ketones, ethers and esters. Glycols such as ethylenglycol and propylenglycol, ketones such as dimethylketone, methylethylketone, ethers such as diisopropylether, methyltercbutylether and tetrahydrofurane, and esters such as methyl acetate and butyl acetate may be used. Specially preferred are alcohols from 1 to 8 carbon atoms such as methanol, ethanol, isopropanol, n-butanol, terc-butanol, cyclohexanol, and the methyl and dimethylhexanols.

According to the invention, the impregnating solution must preferably comprise titanium alkoxyde solutions (with alkoxyde groups containing from 1 to 8 carbon atoms) or titanocene solutions (with cyclopentadienyls or substituted cyclopentadienyls with 5–10 carbon atoms) in an alcohol $C_1$–$C_8$ with titanium concentrations in the range from 0.05 to 10 moles/liter. The titanium concentration of the solution and the amount of the same must be chosen in such a way that the titanium concentration in the final catalyst falls approximately between 0.1 and 10% in weight. The impregnation can be carried out in only one or in several stages, in this latter case, if desired, with intermediate drying and calcination according to known procedures.

In the epoxidation of unsaturated olefinic compounds it may be advisable to incorporate to the catalyst, as promoter, small amounts of alkaline or alkaline-earth metals salts, for instance lithium, sodium, potassium, magnesium or calcium. In order to do so the silica may be previously impregnated in an solution in water or in an organic solvent, of the promoter and, next impregnate the silica with the titanium solution or carry out the impregnation of the silica in one step with a solution of the promoter and of the titanium compound in the oxygenated organic solvent. The amount of promoter to be used is small and generally ranges between 0.01% and 1% in weight (mass of the promoter per each 100 g of catalyst). The function of the promoter is to prevent the oxiranic ring from breaking, which may give rise to undesired products and which are usually catalysed by superficial acid sites on the catalyst, and improve in this matter the specificity as regards the formation of epoxides.

Catalysts prepared according to this invention are specially adequate for the epoxidation in the liquid phase of carbon—carbon double bonds of olefinic compounds by the reaction with hydrogen peroxide.

Carbon—carbon double bonds of olefinic compounds which can be epoxidated according to the invention can be described by the formula:

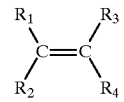

where $R_1$, $R_2$, $R_3$ and $R_4$ may be hydrogen or halogen atoms, alkyl, aryl, cycloalkyl, arylalkyl radicals or carboxylic, ester, anhydro, sulfonic, nitril or ether groups. The alkyl, cycloalkyl, arylallyl, and aryl radicals can also contain carboxylic, ester, sulfonic acid, nitril, halogen, hydroxyl and ketone groups. It can be seen that our invention is applicable to a wide range of olefinic compounds. In general it is possible to epoxidate all olefinic compounds that contain non aromatic double bonds with hydrogen peroxide.

A large group of olefinic groups that are susceptible of epoxidation with hydrogen peroxide according to the invention are the alkenes that contain from 2 to 18 carbon atoms, such as ethylene, propylene, 1-butene, 2-butene, isobutylene, 1-hexene, 1-octene, 1-hexadecene. However, in practice propylene and $C_4$ olefins are preferred.

Cycloalkenes and substituted cycloalkenes constitute another class of olefinic compounds that can be epoxidated according to this invention. Adequate cycloalkenes are for instance cyclopentene, cyclohexene, cyclooctene and cyclododecene. Cyclic olefinic compounds with more than one double bond in their molecule may also be used, such as dicyclopentadiene, cyclooctadiene, and vinylcyclohexene. Alkenes with arylic substituents may also be used, for instance styrene, divinylbenzene, etc. Furthermore, olefinic compounds which due to their large volume cannot be epoxidated with other catalysts of microporous nature for instance norbornene, shall be included.

Olefinic compounds which may be used according to the invention can contain other functional groups directly linked or not to the carbon—carbon double bond. For instance allylic alcohol, and its esters, allyl bromide chloride, acrylic and methacrylic acids and their esters, fumaric and maleic acids and their esters, etc.

Commercial hydrogen peroxide in aqueous solutions of approximately 30% is a standard product in the market but shows the drawback of its relatively high price. However, the process subject matter of the invention has the advantage of the use of hydrogen peroxide diluted solutions in organic solvents. The preferred hydrogen peroxide concentrations are in the range from 1 to 15%. These diluted solutions of hydrogen peroxide in organic solvents can be obtained at a low price, for instance by means of the oxidation with molecular oxygen of secondary alcohols, such as isopropylic alcohol, 1-phenylethanol, alkylhydroanthraquinones, etc., according to known procedures, but preferably as described in the Spanish Patent no. 9603201, and be used directly in the epoxidation of olefinic compounds without the previous purification or extraction of hydrogen peroxide.

The reaction temperature for epoxidation is preferably between 30 and 140° C. (more preferably between 60–100° C.), which are enough to get selective transformations of olefins to epoxide in short reaction times with a minimum non selective break down of the hydrogen peroxide. In general, it is advantageous to carry out the transformation of the hydrogen peroxide as completely as possible, preferably above 90% and more preferably above 95% in order to avoid risks associated to the presence of hydrogen peroxide in the products at the outlet of the reactor, in the epoxide isolation and purification stages. The optimum reaction temperature is determined among other factors by the concentration of the catalyst, the reactivity of the olefinic compound and its concentration, and by the solvent type. In general, times of residence between 10 and 300 minutes are adequate, depending on the above mentioned variables. The reaction is carried out preferably at atmospheric pressure or at high pressure (typically between 0.1 and 10 Mpa) in order to maintain the components of the reaction mixture in the liquid phase. For instance, when an olefin which has a boiling point at atmospheric pressure below the epoxidation reaction temperature, for instance propylene is epoxidated, it is necessary to operate at enough pressure to maintain propylene in the liquid phase.

The epoxidation reaction according to the invention can be carried out discontinuously, semi-continuously, or continuously, using a reactor of the adequate kind, for instance a catalyst fixed bed, a reactor of the stir tank type with a catalyst particle suspension, etc. It is possible to use the generally known methods to carry out epoxidations with hydrogen peroxide with metallic catalysts. Thus, the reactants can be added to the reactor in a combined or sequential manner. For instance, the hydrogen peroxide and/or the olefin can be added increasingly to the reactor.

The epoxidation shall be carried out in the presence of adequate solvents capable of dissolving or dispersing the reactants and facilitate the control of the reaction temperature. The preferred solvents are $C_6$–$C_8$ aromatic alcohols such as 1-phenylethanol, 2-phenylethanol or $C_1$–$C_6$ aliphatic alcohols such as methanol, ethanol, n-butanol, hexanol, but preferably 2-methyl-2-propanol.

Once that the epoxidation reaction has progressed to the desired degree of transformation, the catalyst may be separated out of the reaction mixture by means of different methods known, such as filtration if the catalyst is used suspended in the reaction medium, for its subsequent re-utilisation. When the reaction is carried out continuously it may be desirable to periodically or continuously regenerate all or part of the catalyst used in order to maintain the optimum activity and specificity levels. The adequate regeneration techniques are well known and include, calcination and treatment with solvents. The epoxide can be separated out of the reaction mixture resulting from the separation of the catalyst by means of known methods such as for instance, fractional distillation, extractive distillation, liquid—liquid extraction, etc.

With the above description any expert can establish the essential characteristics of the invention, introduce the changes and modifications in order to adapt it to the epoxidation of olefins under different conditions without deviating from the spirit and objective of the same.

EXAMPLES

Example 1

A titanium catalyst was prepared on silica according to the following procedure: 1.43 g of isopropyl orthotitanoate were added to 300 ml of 1-hexanol, were placed under stirring, and the mixture was heated to 1500C, next 9 g of Grace silica were added (specific surface of 210 m$^2$/g and a pore volume of 1.43 cm$^3$/g), the shaking and the temperature were maintained for 2 h. It was allowed to cool off and it was filtered by washing the solid with the solvent used in the preparation. Lastly, it was calcinated at 5000C for 5 h.

Example 2

A catalyst was prepared proceeding in the same manner as in example 1, but 1-phenylethanol was used as the solvent instead of 1-hexanol.

Example 3

A catalyst was prepared proceeding in the same manner as in example 1, but cyclohexanol was used as the solvent instead of 1-hexanol. This catalyst was named Ti/SiO$_2$.

Comparative Example 1

A catalyst was prepared proceeding in the same manner as in example 1, but toluene, a non oxygenated solvent, was used as the solvent instead of 1-hexanol.

Comparative Example 1b

A titanium catalyst was prepared on silica using TiF$_4$ as a titanium precursor according to the method described in example 1 of the patent WO 94/23834. The titanium content of the solid was 1.2% in weight. This catalyst was named TiF$_4$/SiO$_2$.

Comparative Example 1c

A titanium catalyst was prepared on silica using TiCl$_4$ as a titanium precursor according to the method described in example 1 of the patent U.S. Pat. No. 3,923,843. The titanium content of the solid was 1.2% in weight. This catalyst was named TiCl/SiO$_2$.

Examples 4–7

The catalysts of the examples 1 through 3 and the comparative 1 were tested in the epoxidation reaction of 1-octene with hydrogen peroxide. 0.2 moles of olefin, 11 g of 1-phenylethanol and 1 g of catalyst were introduced into the reactor. The mixture was heated to 80° C. and 4 g of a 6% wt. solution of $H_2O_2$ in 1-phenylethanol were added drop by drop for 30 minutes. The results obtained after one hour of reaction from the beginning of the addition of hydrogen peroxide are shown in Table 1, from which the need to use an oxygenated organic solvent in the synthesis of the catalysts can be inferred.

TABLE 1

Effect of the solvent used in the synthesis of the catalyst on the behaviour on the epoxidation reaction of 1-octene (1 h) (reaction conditions in the text).

| Example | Solvent in the Synthesis | % $H_2O_2$ Trans. | % Spe. Epoxide | % Spe. Acetophenone |
|---|---|---|---|---|
| 4 | Toluene | 97 | 36 | 17 |
| 5 | 1-Hexanol | 96 | 53 | 8 |
| 6 | 1-Phenylethanol | 98 | 56 | 6 |
| 7 | Cyclohexanol | 98 | 68 | 6 |

Example 8

The catalyst prepared in example 3 was used in the epoxidation of norbornene, a voluminous olefin which cannot be epoxidated on TS-1. 0.2 moles of olefin, 10.4 g of diglyme and 1 g of catalyst were introduced into the reactor. The mixture was heated to 80° C. and 4.36 g of a hydrogen peroxide solution obtained from 0.36 g of a 70% wt. solution of $H_2O_2$ in water and 4 g of diglyme were added drop by drop for 30 minutes. After reacting for one hour from the beginning of the addition of the hydrogen peroxide, a peroxide transformation of 93% and a specificity for epoxide of 98% were obtained.

Example 9

The catalyst in example 3 ($Ti/SiO_2$) was tested in the epoxidation reaction of cyclohexene with hydrogen peroxide. 0.2 moles of olefin, 10.4 g of diglyme and 1 g of catalyst were introduced into the reactor. The mixture was heated to 80° C. and 4.36 g of a hydrogen peroxide solution obtained from 0.36 g of a 70% wt. solution of $H_2O_2$ in water and 4 g of diglyme were added drop by drop for 30 minutes. After reacting for one hour from the beginning of the addition of the hydrogen peroxide, a peroxide transformation of 90% and a specificity for epoxide of 77% were obtained. Table 2.

Comparative Example 9

We proceeded as in example 9, but using the catalyst prepared as in the comparative example 1. The results obtained, presented in table 2, show that the catalyst of the present invention is more active and specific for epoxide than those used in the prior art.

TABLE 2

Epoxidation of cyclohexene at 80° C. (reaction for 1 h), reaction conditions of example 9.

| Example | Catalyst | % $H_2O_2$ Trans. | % Spe. Epoxide | % Spe. Diol | % Spe. Other |
|---|---|---|---|---|---|
| 9 | $Ti/SiO_2$ (Examp. 3) | 90 | 77 | 16 | 7 |
| Comparative | $TiF/SiO_2$ | 84 | 60 | 36 | 2 |

TABLE 2-continued

Epoxidation of cyclohexene at 80° C. (reaction for 1 h), reaction conditions of example 9.

| Example | Catalyst | % $H_2O_2$ Trans. | % Spe. Epoxide | % Spe. Diol | % Spe. Other |
|---|---|---|---|---|---|
| 9 | (Comparative 1b) | | | | | other = 3-cyclohexen-1-ol

Example 10

The catalyst $Ti/SiO_2$ (prepared according to example 3) was tested in the epoxidation reaction of 1-octene with hydrogen peroxide. 0.2 moles of olefin, 11 g of 2-methyl-2-propanol and 1 g of catalyst were introduced into the reactor. The mixture was heated to 80° C. and 4 g of a 6% wt. solution of $H_2O_2$ in 1-phenylethanol were added drop by drop for 30 minutes. After one hour of reaction from the beginning of the addition of the hydrogen peroxide, a transformation of $H_2O_2$ of 97% and a specificity for epoxide of 95% were obtained. Table 3.

Comparative Example 10

Proceeding in a manner identical to example 10 but using the catalyst in the comparative example 1b, the epoxidation of 1-octene was carried out. The results obtained after 1 h of reaction are shown in table 3. The catalyst of the present invention is more active and specific for epoxide than those used in the prior art (WO 94/23834).

Comparative Example 10b

Proceeding in a manner identical to example 10 but using the catalyst in the comparative example 1c, the epoxidation of 1-octene was carried out. The results obtained after 1 h of reaction and shown in table 3, prove that the catalyst of the present invention is more active and specific for epoxide than those used in the prior art.

TABLE 3

Epoxidation of 1-octene (reaction for 1 hour) reaction conditions of example 11.

| Example | Catalyst | % $H_2O_2$ Trans. | % Spe. Epoxide | % Spe. Other | % Spe. ACP |
|---|---|---|---|---|---|
| 10 | $Ti/SiO_2$ (Examp. 3) | 97 | 95 | 2 | 0 |
| Comparative 10 | $TiF/SiO_2$ (Comparative 1b) | 76 | 65 | 4 | 7 |
| Comparative 10b | $TiCl/SiO_2$ (Comparative 1c) | 91 | 68 | 1 | 3 |

Other = compounds from the breaking of the oxirane ring (glycol and ether glycol)
ACP = acetophenone

Example 11

A hydrogen peroxide solution was prepared by the oxidation of 1-phenilethanol as described in example 11 of the Spanish Patent no. 9603201. This solution with a $H_2O_2$ content of 4.24% wt. was used in the epoxidation of 1-octene without any kind of previous purification. 0.2 moles of olefin, 11 g of 2-methyl-2-propanol and 1 g of catalyst prepared according to example 3 were introduced into the reactor. The mixture was heated to 80° C. and 6 g of the $H_2O_2$ solution were added drop by drop for 30 minutes. The transformation of $H_2O_2$ obtained was of 95% and the specificity for epoxide of 97%, after one hour of reaction, from the beginning of the addition of the hydrogen peroxide.

Example 12

30 g of catalyst were prepared from a grace silica (Grace SP9.10214, with a specific surface of 301 m²/g). 5.85 g of isopropyl orthotitanoate were added to 900 ml of cyclohexanol, they were placed under stirring, and the mixture was heated to 150° C., next 30 g of silica were added The shaking and the temperature were maintained for 2 h. It was allowed to cool off and it was filtered by washing the solid with the solvent used in the preparation, lastly it was calcinated at 500° C. for 5 h. This catalyst was tested in the epoxilation reaction of propylene with hydrogen peroxide. In order to do so, a stirring tank discontinuous reactor with basket was used to work with the solid catalyst, 12 g were introduced in the basket thereof and the rest of the volume of the latter was filled with glass beads. Next 192 g of 2-methyl-2-propanol and 147.2 g of propylene and the mixture, under stirring, was heated to reach the reaction temperature, 70° C. At that point, nitrogen was introduced until a pressure of 34 Mpa was reached, in order to ensure that propylene is in the liquid phase. The reactive mixture was added with 104 g of a 3.2% wt. solution of hydrogen peroxide in MEA and 2-methyl-2-propanol for 30 minutes. After one hour of reaction, from the beginning of the addition of the hydrogen peroxide, a transformation of $H_2O_2$ of 96.5% and a specificity for epoxide of 92% were obtained.

What is claimed is:

1. Liquid phase epoxidation procedure in the liquid phase of carbon—carbon double bonds of olefinic compounds with hydrogen peroxide in the presence of solvents, at temperatures ranging between approximately 50° and 140° C., characterised in that the use of silica supported titanium catalyst, in which said catalysts are prepared by the impregnation of silicas with a specific surface ranging between 50 and 900 m²/g with solutions of titanium alkoxydes and/or titanocenes in oxygenated organic solvents, followed by the separation of the excess solution and of the solvent.

2. Procedure according to claim 1 characterised in that the oxygenated organic solvent is a $C_1$–$C_8$ alcohol.

3. Procedure according to claim 2 characterised in that the catalyst is added, by means of impregnation, with alkaline or alkaline-earth metals salts in amounts ranging between approximately 0.01 and 0.1% in weight (weight of alkaline or alkaline-earth metals per 100 g of catalyst).

4. Procedure according to claim 3 characterised in that it uses hydrogen peroxide solutions in organic solvents with concentrations ranging between approximately 1 and 15% in weight.

5. Procedure according to claim 4 characterised in that it uses hydrogen peroxide solutions obtained by means of the oxidation of secondary alcohols with molecular oxygen or air.

6. Procedure according to claim 5 characterised in that the olefinic compound is an alkene or a cycloalkene.

7. Procedure according to claim 6 characterised in that the alkene is propylene.

8. Procedure according to claim 6 characterised in that the cycloalkene is cyclohexene.

9. Procedure according to claim 6 characterised in that the olefinic compound is an allylic alcohol.

10. Procedure according to claim 6 characterised in that the olefinic compound is fumaric acid or maleic acid or one of its esters, anhydrides or mixtures thereof.

11. Procedure according to claim 10 characterised in that $C_6$–$C_9$ aromatic alcohols or $C_1$–$C_6$ aliphatic alcohols are used in the epoxidation reaction as solvents.

12. Procedure according to claim 11 characterised in that the organic solvent is 2-methyl-2-propanol or mixtures of organic solvents containing 2-methyl-2-propanol.

13. A process for the liquid phase epoxidation of olefinic compounds comprising combining an olefinic compound with catalyst and hydrogen peroxide in the presence of solvent and at a temperature of approximately 50° C. to 140° C. and thereafter separating the excess solution and solvent wherein the catalyst is prepared by impregnating silica having a surface area of between 40 and 900 m²/g with a solution of titanium alkoxydes and/or titanocenes in oxygenated organic solvents.

14. The process of claim 13 wherein the catalyst is impregnated with alkaline or alkaline earth metal salts in amounts ranging between approximately 0.01 and 0.1% in weight (weight of alkaline or alkaline earth metals per 100 g of catalyst).

15. The process of claim 13 wherein the oxygenated solvent is a $C_1$ to $C_8$ alcohol.

16. The process of claim 13 wherein the hydrogen peroxide is obtained by oxidation of secondary alcohols with molecular oxygen or air.

17. The process of claim 13 wherein the olefinic compound is an alkene, an allylic alcohol or a cycloalkene.

18. The process of claim 13 wherein the olefinic compound is propylene, cyclohexene, fumaric acid, maleic acid, or an ester or an anhydride of fumaric or maleic acid, or mixtures thereof.

19. The process of claim 13 wherein the solvents are $C_6$ to $C_9$ aromatic alcohols or $C_1$ to $C_6$ aliphatic alcohols.

20. The process of claim 13 wherein the solvent comprises 2-methyl-2-propanol.

* * * * *